United States Patent [19]
Triller

[11] Patent Number: 5,198,845
[45] Date of Patent: Mar. 30, 1993

[54] APPARATUS FOR PRODUCING AN IMAGE OF AN OBJECT (III)

[75] Inventor: Adolf Triller, Lochham, Fed. Rep. of Germany

[73] Assignee: G. Rodenstock Instrument GmbH, Ottobrunn-Riemerling, Fed. Rep. of Germany

[21] Appl. No.: 459,694
[22] PCT Filed: Jun. 29, 1989
[86] PCT No.: PCT/DE89/00434
§ 371 Date: Jul. 2, 1990
§ 102(e) Date: Jul. 2, 1990
[87] PCT Pub. No.: WO90/00026
PCT Pub. Date: Jan. 11, 1990

[30] Foreign Application Priority Data

Jun. 29, 1988 [DE] Fed. Rep. of Germany ....... 3821973

[51] Int. Cl.$^5$ ............................. A61B 3/10; A61B 3/02
[52] U.S. Cl. .................... 351/221; 351/205; 351/237
[58] Field of Search ............ 351/205, 206, 207, 208, 351/211, 221, 237; 350/6.6, 6.8; 359/212, 205, 206, 207

[56] References Cited
U.S. PATENT DOCUMENTS 4,447,112 5/1984 Matsuoka .......................... 359/212
4,781,453 11/1988 Kobayashi ...................... 351/221 X
4,838,679 6/1989 Bille ................................ 351/221 X Primary Examiner—Rodney B. Bovernick
Attorney, Agent, or Firm—Antonelli, Terry, Stout & Kraus

[57] ABSTRACT

Disclosed is an apparatus for producing an image of an object and, in particular, for examining the eye, having an illumination light source, the light of which can be focussed onto the section of the object to be examined, a scanning device, which generates a scanning movement of the source of the illumination light over the section of the object to be examined and which is provided with image forming optical elements in addition to the scanning movement producing elements, a detector device, which receives the light reflected from the section of the object to be examined, and an evaluation and sychronization unit, which produces an image of the section of the object from the time-sequential output signal from the detector device. The invention has at least one aspherical element which compensates for trapezoidal distortion.

15 Claims, 1 Drawing Sheet

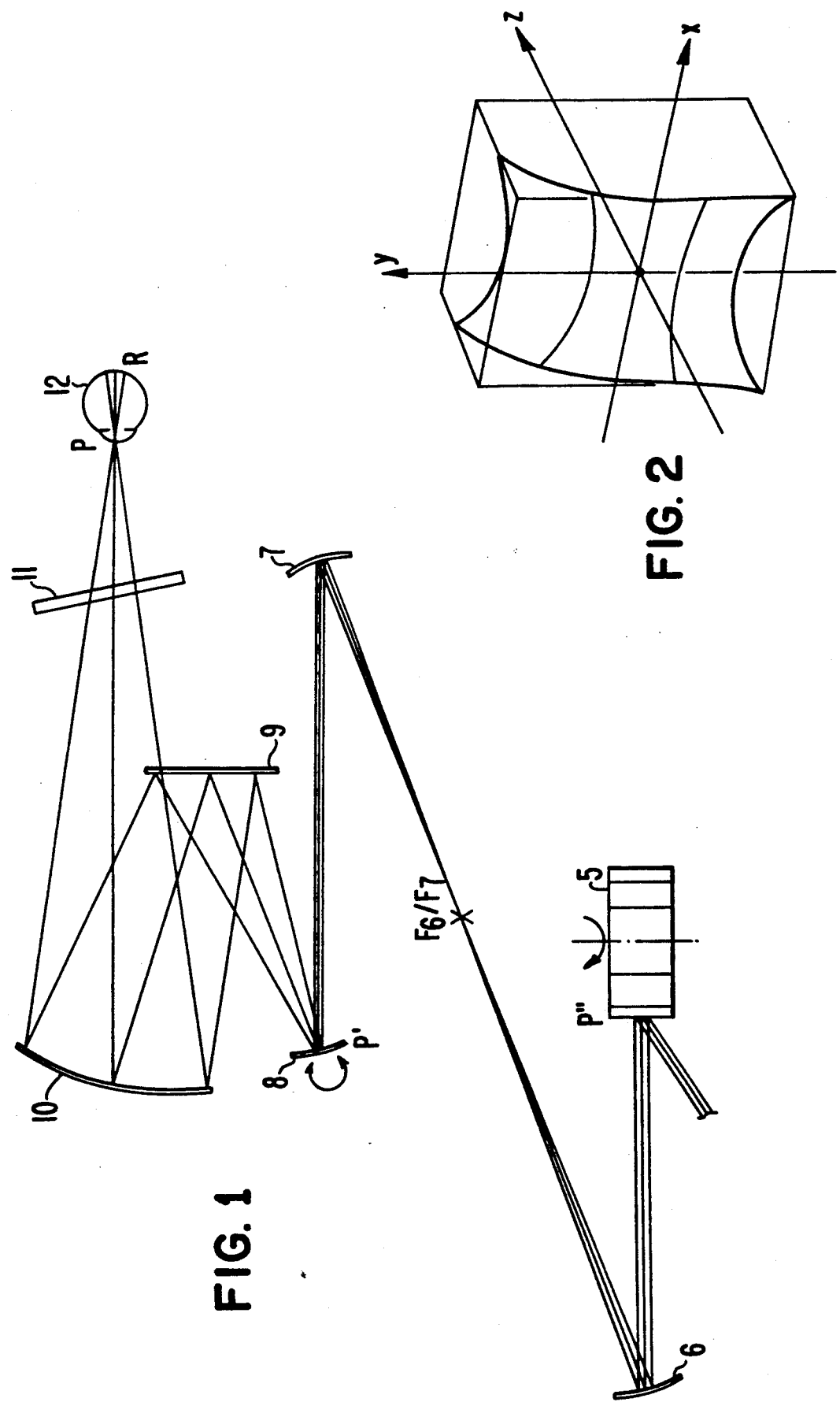

APPARATUS FOR PRODUCING AN IMAGE OF AN OBJECT (III)

DESCRIPTION

1. Technical Field

The present invention relates to an apparatus for producing an image of an object and, in particular, for examining the eye.

2. State of the Art

The difficulty in examining the posterior portion of the eye is that the illumination and the examination have to be conducted through the pupil and the optically often not clear anterior media of the eye, in which reflexes occur and which cause aberrations.

For some time, therefore, it has been recommended to employ scanning devices that do not illuminate large areas of the posterior portion of the eye, but scan the posterior portion of the eye with as small as possible an illumination beam and note the reflected light in correlation to the scanning sequence instead of using conventional fundus cameras. Reference with regard to this is made, by way of illustration, to "The Foundations of Ophthalmology", Vol. 7, pp. 307/308, 1962, U.S. Pat. No. 4,213,678, Japanese patent publications 61-5730 and 50-138822 and EP-A-0145 563.

The state of the art devices for examining the eye therefore have a number of disadvantages:

By tilting the elements forming the scanning beam and the reflected light, respectively the scattered light beam toward each other and by deflecting the beam two-dimensionally, which is necessary for the x/y scanning motion, the scale of the imaging is not constant over the area of the image.

This results in a rectangle being distorted trapezoidally, which is particularly disturbing if, by way of illustration, an electronic image assessment of sequentially shot areas are to be "adjoined".

Description of the Invention

The object of the present invention is to further improve an apparatus for obtaining an image and, in particular, for examining the eye in such a manner that the trapezoidal distortion is conpensated for.

A solution to the aforegoing object and its further embodiments are set forth in the patent claims hereto.

In accordance with the present invention, the aforegoing object was solved by providing at least one aspherical element, which compensates for the trapezoidal distortion, in the beam path between the scanning elements and the object, of which the image is to be made.

One embodiment of the present invention is provided with an additional aspherical element, which bundles the image in the pupil plane of the eye; the first aspherical element then compensates for the trapezoidal distortion in the plane of the second element.

By way of illustration, in ophthalmological applications, the bundle of rays is usually bundled in the pupil of the eye. As this bundling of rays in the image of the pupil has to be taken into account, it is advantageous to provide a second aspherical element, which yields an additional degree of freedom in correction.

The first element brings about a distortion correction in the plane of the second element. The second element then ensures an exact bundling of rays in the image of the pupil.

If both the distortion correction in the image of the pupil and the bundling of rays in the pupil plane are fulfilled, the bundle of rays corrects the distortion in all other plane section images.

Furthermore, it is preferable if the refractive power of both aspherical elements is practically zero in the region of the optical axis.

BRIEF DESCRIPTION OF THE DRAWING

The present invention is made more apparent in the following section using a preferred embodiment with reference to the accompanying drawing, in which:

FIG. 1 depicts a section through a part of an invented apparatus, and

FIG. 2 schematically depicts a correction surface.

DESCRIPTION OF A PREFERRED EMBODIMENT

The invented apparatus illustrated in sections in FIG. 1 is provided with a not depicted illumination light source, by way of illustration a laser, and a not depicted detector device, the output signal of which is assessed by an evaluation and synchronization unit and, by way of illustration represented on a monitor. In the illustrated preferred embodiment both the illumination beam 14 and the light beam 15 coming from the fundus oculi "run" via the deflection device.

The light beam 14 from the laser is deflected in a horizontal direction (perpendicular to the drawing plane) by a first deflecting element (horizontal scanner), which, in the illustrated preferred embodiment, is a rotating polygonal mirror 5. The beam fanning out in the horizontal plane runs through mirror system 6 and 7 and hits a second deflecting element (vertical scanner), which, in the illustrated embodiement, is an oscillating, respectively a galvanometer, mirror 8. Behind mirror 8, the bundle of rays has a "rectangular" cross-section. Following deflection at a plane mirror 9, which is described below, its image is projected by a concave mirror 10 onto the eye to be examined 12 via an element 11, which is also described below. The reflected ray of light 15 runs through the mentioned elements in reverse order and is indicated behind the horizontal deflecting element 5 by a not depicted detector after prior separation of the illumination and the examination light path.

An element of the present invention is that it was understood that a trapezoidal distortion would result with an apparatus according to FIG. 1. This trapezoidal distortion is corrected by the invented design of elements 9 and 11, which will be described in the following section.

For this purpose, the first element, by way of illustration element 9, brings about a correction of the trapezoidal distortion in the plane of the second element, by way of illustration element 11. The second element then ensures an exact bundling of rays in pupil image P.

If both the distortion correction in the pupil image and the bundling of rays in the pupil plane is fulfilled, the bundel of rays corrects the distortion in all other plane section images.

In the case of the approximately 1:1 imaging of the pupil illustrated in FIG. 1, it is preferable if the elements 9, respectively 11, have aspherical surfaces, the optical power of which is practically zero in the center, i.e. in the region of the optical axis. Proceeding from this point of reference, the surfaces along the reflection plane of the concave mirror pass on the one side into a convex curvature and on the other side into a concave curvature, the size of which is made to comply with the required distortion correction, which is schematically depicted in FIG. 2, which shows the system of coordinates x,y,z used in the following section.

The surface may, by way of illustration, respond to the function F:

$$F = \Gamma*(x^2+z^2) - 2z = 0$$

wherein $\Gamma$ is the reciprocal value of the radius of the transverse curves Q and is dependent on y. The coordinates lie in the reflection plane of element 9. With the following dependence of the curvature $\Gamma$ on y:

$$\Gamma = c_1 y + c_2 y^2 + c_3 y^3$$

yields, by way of illustration, the following surface function:

$$F = (c_1 y + c_2 y^2 + c_3 y^3)*(x^2+z^2) - 2z = 0$$

In the preceding equations the connecting line of the apex of the transverse curves Q lies on the y-axis. If a curvature is introduced, pertinently following a curve of the third order, as an "extended" surface function is yielded:

$$F = (c_1 y + c_2 y^2 + c_3 y^3)*(x^2+z^2-2zy^3 c_4) - 2z + 2y^3 c_4 = 0$$

The curvature of the connecting line of the apex can be controlled via the constant $c_4$.

The equations given in the preceding section also are valid for element 11, which may be a plane parallel plate, the "plane surface" of which, by way of illustration, is "aspherically modified" according to the preceding equations.

By means of the appropriate selection of the values $c_i$, i=1,2,3,4, the conditions cited in the preceding section—distortion correction in the image of the pupil and exact bundling of rays in the pupil plane—can be fulfilled so that the bundle of rays corrects all the other plane section images.

In the preceding section, the present invention has been described using a preferred embodiment without the intention of limiting the scope of the overall inventive concept and, in particular, without the intention of limiting the general applicability of the apparatus described in the foregoing, by way of illustration, for ophthalmological purposes.

What is claimed is:

1. An apparatus for producing an image of an object, comprising:
   light source means for producing light for illuminating an object;
   scanning means, including at least one image-forming element and at least one scanning element, for focusing the light produced by the light source means on the object and for scanning the focused light across the object, the scanning means producing trapezoidal distortion in the focused light scanned across the object; and
   trapezoidal distortion correction means, including at least one aspherical element disposed between the at least one scanning element and the object, for correcting the trapezoidal distortion produced by the scanning means, wherein a refractive power of the at least one aspherical element is substantially zero near an optical axis of the at least one aspherical element;
   wherein the object reflects the focused light scanned across the object, and wherein the apparatus further comprises:
   detecting means for detecting the light reflected from the object and for producing an output signal representing the detected light; and
   imaging means for producing an image of the object from the output signal of the detecting means.

2. An apparatus according to claim 1, wherein the at least one aspherical element includes a first aspherical element and a second aspherical element, and wherein the first aspherical element corrects trapezoidal distortion in a plane of the second aspherical element.

3. An apparatus according to claim 2, wherein respective refractive powers of the first and second aspherical elements are substantially zero near respective optical axes of the first and second aspherical elements.

4. An apparatus according to claim 2, wherein the first aspherical element is a mirror.

5. An apparatus according to claim 2, wherein the at least one imaging-forming element includes a concave mirror, and wherein the first and second aspherical elements are disposed on opposite sides of the concave mirror along an optical path of the apparatus.

6. An apparatus according to claim 5, wherein a distance between the first aspherical element and the concave mirror is substantially equal to a distance between the second aspherical element and the concave mirror.

7. An apparatus for producing an image of an object, comprising:
   light source means for producing light for illuminating an object;
   scanning means, including at least one image-forming element and at least one scanning element, for focusing the light produced by the light source means on the object and for scanning the focused light across the object, the scanning means producing trapezoidal distortion in the focused light scanned across the object; and
   trapezoidal distortion correction means, including at least one aspherical element disposed between the at least one scanning element and the object, for correcting the trapezoidal distortion produced by the scanning means.

8. An eye-examining apparatus for producing an image of an eye, comprising:
   light source means for producing light for illuminating an eye;
   scanning means, including at least one image-forming element and at least one scanning element, for focusing the light produced by the light source means on the eye and for scanning the focused light across the eye, the scanning means producing trapezoidal distortion in the focused light scanned across the eye; and
   trapezoidal distortion correction means, including at least one aspherical element disposed between the at least one scanning element and the eye, for correcting the trapezoidal distortion produced by the scanning means.

9. An eye-examining apparatus according to claim 8, wherein the eye reflects the focused light scanned across the eye, and wherein the apparatus further comprises:

detecting means for detecting the light reflected from the eye and for producing an output signal representing the detected light; and imaging means for producing an image of the eye from the output signal of the detecting means.

10. An eye-examining apparatus according to claim 8, wherein a refractive power of the at least one aspherical element is substantially zero near an optical axis of the at least one aspherical element.

11. An eye-examining apparatus according to claim 8, wherein the at least one aspherical element includes a first aspherical element and a second aspherical element, and wherein the first aspherical element corrects trapezoidal distortion in a plane of the second aspherical element.

12. An eye-examining apparatus according to claim 11, wherein respective refractive powers of the first and second aspherical elements are substantially zero near respective optical axes of the first and second aspherical elements.

13. An eye-examining apparatus according to claim 11, wherein the first aspherical element is a mirror.

14. An eye-examining apparatus according to claim 11, wherein the at least one imaging-forming element includes a concave mirror, and wherein the first and second aspherical elements are disposed on opposite sides of the concave mirror along an optical path of the apparatus.

15. An eye-examining apparatus according to claim 14, wherein a distance between the first aspherical element and the concave mirror is substantially equal to a distance between the second aspherical element and the concave mirror.

* * * * *